(12) United States Patent
Starkebaum et al.

(10) Patent No.: US 8,406,901 B2
(45) Date of Patent: Mar. 26, 2013

(54) SUTURELESS IMPLANTABLE MEDICAL DEVICE FIXATION

(75) Inventors: Warren L. Starkebaum, Plymouth, MN (US); Daniel J. Stetson, Lino Lakes, MN (US); Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 1815 days.

(21) Appl. No.: 11/413,071

(22) Filed: Apr. 27, 2006

(65) Prior Publication Data
US 2007/0255295 A1 Nov. 1, 2007

(51) Int. Cl.
*A61N 1/05* (2006.01)

(52) U.S. Cl. .......................... 607/130; 607/126

(58) Field of Classification Search .............. 607/126, 607/128, 129–133, 149, 40, 115–119; 606/129; 600/372–375, 377, 381, 386
See application file for complete search history.

(56) References Cited

U.S. PATENT DOCUMENTS

| | | | |
|---|---|---|---|
| 4,035,909 A | 7/1977 | Dey | |
| 4,103,690 A * | 8/1978 | Harris | 607/128 |
| 4,112,952 A * | 9/1978 | Thomas et al. | 607/128 |
| 4,376,811 A | 3/1983 | Goebel | |
| 4,731,305 A | 3/1988 | Goebel et al. | |
| 5,002,067 A | 3/1991 | Berthelsen et al. | |
| 5,024,239 A | 6/1991 | Rosenstein | |
| 5,249,574 A * | 10/1993 | Bush et al. | 607/9 |
| 5,255,678 A | 10/1993 | Deslauriers et al. | |
| 5,255,679 A | 10/1993 | Imran | |
| 5,265,608 A | 11/1993 | Lee et al. | |
| 5,282,845 A | 2/1994 | Bush et al. | |
| 5,306,581 A | 4/1994 | Taylor et al. | |
| 5,314,462 A * | 5/1994 | Heil et al. | 607/128 |
| 5,358,514 A | 10/1994 | Schulman et al. | |
| 5,383,922 A | 1/1995 | Zipes et al. | |
| 5,387,233 A | 2/1995 | Alferness et al. | |
| 5,492,119 A * | 2/1996 | Abrams | 600/375 |
| 5,540,734 A | 7/1996 | Zabara | |
| 5,545,219 A | 8/1996 | Kuzma | |
| 5,766,234 A * | 6/1998 | Chen et al. | 607/92 |

(Continued)

FOREIGN PATENT DOCUMENTS

| | | |
|---|---|---|
| WO | WO 02/30295 A1 | 4/2002 |
| WO | 2009039400 A1 | 3/2009 |

(Continued)

OTHER PUBLICATIONS

International Search Report and Written Opinion dated Jul. 18, 2007 for corresponding PCT Application No. PCT/US2007/001886, (14 pgs.).

(Continued)

*Primary Examiner* — Carl H Layno
*Assistant Examiner* — Jessica Sarcione

(57) ABSTRACT

A device comprises a medical implant and an actively deployable clip attached to the medical implant that operates to restrict movement of the medical implant once the actively deployable clip is deployed within a body of a patient. In some embodiments, the medical implant is an electrical lead for electrical stimulation. The actively deployable clip is operable to fixate the medical implant to a body tissue once deployed, such that the actively deployable clip performs a similar function to a suture. In this manner, embodiments of the invention may provide a medical implant that requires few or even no sutures to properly fixate the implant within the patient.

32 Claims, 6 Drawing Sheets

U.S. PATENT DOCUMENTS

| | | | |
|---|---|---|---|
| 5,776,632 A | 7/1998 | Honegger | |
| 5,814,089 A | 9/1998 | Stokes et al. | |
| 5,840,076 A | 11/1998 | Swanson et al. | |
| 5,860,974 A | 1/1999 | Abele | |
| 5,897,584 A | 4/1999 | Herman | |
| 6,074,401 A | 6/2000 | Gardiner et al. | |
| 6,113,593 A | 9/2000 | Tu et al. | |
| 6,136,005 A | 10/2000 | Goode et al. | |
| 6,149,658 A | 11/2000 | Gardiner et al. | |
| 6,183,305 B1 | 2/2001 | Doan et al. | |
| 6,238,813 B1 | 5/2001 | Maile et al. | |
| 6,266,568 B1 | 7/2001 | Mann et al. | |
| 6,308,105 B1 | 10/2001 | Duysens et al. | |
| 6,350,278 B1 | 2/2002 | Lenker et al. | |
| 6,352,561 B1 | 3/2002 | Leopold et al. | |
| 6,434,431 B1 | 8/2002 | Camps et al. | |
| 6,468,301 B1 | 10/2002 | Amplatz et al. | |
| 6,477,423 B1* | 11/2002 | Jenkins | 607/40 |
| 6,498,951 B1 | 12/2002 | Larson et al. | |
| 6,505,075 B1 | 1/2003 | Weiner | |
| 6,510,332 B1* | 1/2003 | Greenstein | 600/377 |
| 6,514,265 B2 | 2/2003 | Ho et al. | |
| 6,529,777 B1 | 3/2003 | Holmström et al. | |
| 6,551,332 B1 | 4/2003 | Nguyen et al. | |
| 6,585,634 B1 | 7/2003 | Henckel et al. | |
| 6,589,238 B2 | 7/2003 | Edwards et al. | |
| 6,600,955 B1 | 7/2003 | Zierhofer | |
| 6,607,541 B1 | 8/2003 | Gardiner et al. | |
| 6,607,843 B2 | 8/2003 | Ruth, II et al. | |
| 6,613,059 B2 | 9/2003 | Schaller et al. | |
| 6,626,916 B1 | 9/2003 | Yeung et al. | |
| 6,641,593 B1 | 11/2003 | Schaller et al. | |
| 6,695,859 B1 | 2/2004 | Golden et al. | |
| 6,876,885 B2 | 4/2005 | Swoyer et al. | |
| 6,889,093 B1 | 5/2005 | Flammang | |
| 6,895,283 B2 | 5/2005 | Erickson et al. | |
| 6,913,607 B2 | 7/2005 | Ainsworth et al. | |
| 6,918,917 B1 | 7/2005 | Nguyen et al. | |
| 6,921,407 B2 | 7/2005 | Nguyen et al. | |
| 6,926,730 B1 | 8/2005 | Nguyen et al. | |
| 6,932,837 B2 | 8/2005 | Amplatz et al. | |
| 6,960,221 B2 | 11/2005 | Ho et al. | |
| 7,047,084 B2 | 5/2006 | Erickson et al. | |
| 7,054,692 B1 | 5/2006 | Whitehurst et al. | |
| 7,070,881 B2 | 7/2006 | Kishiyama et al. | |
| 7,072,703 B2 | 7/2006 | Zhang et al. | |
| 7,099,718 B1 | 8/2006 | Thacker et al. | |
| 7,128,765 B2 | 10/2006 | Paulot et al. | |
| 7,177,702 B2 | 2/2007 | Wallace et al. | |
| 7,181,288 B1 | 2/2007 | Rezai et al. | |
| 7,288,096 B2 | 10/2007 | Chin | |
| 7,291,186 B2 | 11/2007 | Zhang | |
| 7,410,512 B2 | 8/2008 | Tsukamoto et al. | |
| 7,765,014 B2 | 7/2010 | Eversull et al. | |
| 7,797,053 B2 | 9/2010 | Atkinson et al. | |
| 2001/0002300 A1 | 5/2001 | Tinker et al. | |
| 2001/0047181 A1 | 11/2001 | Ho et al. | |
| 2002/0010490 A1 | 1/2002 | Schaller et al. | |
| 2002/0103521 A1 | 8/2002 | Swoyer et al. | |
| 2002/0111659 A1 | 8/2002 | Davis et al. | |
| 2002/0147485 A1 | 10/2002 | Mamo et al. | |
| 2002/0156513 A1 | 10/2002 | Borkan | |
| 2002/0198572 A1 | 12/2002 | Weiner | |
| 2003/0036790 A1 | 2/2003 | Corbett, III et al. | |
| 2003/0069623 A1 | 4/2003 | Stypulkowski | |
| 2003/0078603 A1 | 4/2003 | Schaller et al. | |
| 2003/0088301 A1 | 5/2003 | King | |
| 2003/0093118 A1* | 5/2003 | Ho et al. | 606/224 |
| 2003/0093130 A1 | 5/2003 | Stypulkowski | |
| 2003/0120328 A1 | 6/2003 | Jenkins et al. | |
| 2003/0199974 A1 | 10/2003 | Lee et al. | |
| 2004/0059393 A1 | 3/2004 | Policker et al. | |
| 2004/0093053 A1 | 5/2004 | Gerber et al. | |
| 2004/0101746 A1 | 5/2004 | Ota et al. | |
| 2004/0102797 A1 | 5/2004 | Golden et al. | |
| 2004/0111099 A1 | 6/2004 | Nguyen et al. | |
| 2004/0111139 A1 | 6/2004 | McCreery | |
| 2004/0116878 A1 | 6/2004 | Byrd et al. | |
| 2004/0116992 A1* | 6/2004 | Wardle et al. | 607/116 |
| 2004/0176782 A1 | 9/2004 | Hanse et al. | |
| 2004/0185337 A1 | 9/2004 | Ishizaki | |
| 2004/0193229 A1 | 9/2004 | Starkebaum et al. | |
| 2004/0230279 A1 | 11/2004 | Cates et al. | |
| 2004/0243206 A1 | 12/2004 | Tadlock | |
| 2005/0015129 A1 | 1/2005 | Mische | |
| 2005/0021054 A1 | 1/2005 | Ainsworth et al. | |
| 2005/0060014 A1 | 3/2005 | Swoyer et al. | |
| 2005/0065601 A1 | 3/2005 | Lee et al. | |
| 2005/0070924 A1 | 3/2005 | Schaller et al. | |
| 2005/0090884 A1 | 4/2005 | Honeck | |
| 2005/0096718 A1 | 5/2005 | Gerber et al. | |
| 2005/0102006 A1 | 5/2005 | Whitehurst et al. | |
| 2005/0107861 A1 | 5/2005 | Harris et al. | |
| 2005/0149141 A1 | 7/2005 | Starkebaum | |
| 2005/0149142 A1 | 7/2005 | Starkebaum | |
| 2005/0154321 A1 | 7/2005 | Wolinsky et al. | |
| 2005/0209653 A1 | 9/2005 | Herbert et al. | |
| 2005/0222632 A1 | 10/2005 | Obino | |
| 2005/0245986 A1 | 11/2005 | Starkebaum | |
| 2005/0246004 A1 | 11/2005 | Cameron et al. | |
| 2006/0057458 A1 | 3/2006 | O'Dea et al. | |
| 2006/0069422 A9 | 3/2006 | Bolduc et al. | |
| 2006/0079943 A1 | 4/2006 | Narciso, Jr. | |
| 2006/0079950 A1 | 4/2006 | Lehnhardt et al. | |
| 2006/0085041 A1 | 4/2006 | Hastings et al. | |
| 2006/0085971 A1 | 4/2006 | Andrews et al. | |
| 2006/0206163 A1 | 9/2006 | Wahlstrand et al. | |
| 2006/0206165 A1 | 9/2006 | Jaax et al. | |
| 2006/0206166 A1 | 9/2006 | Weiner | |
| 2006/0222942 A1 | 10/2006 | Zhao et al. | |
| 2006/0241733 A1 | 10/2006 | Zhang et al. | |
| 2006/0271137 A1 | 11/2006 | Stanton-Hicks | |
| 2006/0275659 A1 | 12/2006 | Kim et al. | |
| 2007/0027514 A1 | 2/2007 | Gerber | |
| 2007/0027515 A1 | 2/2007 | Gerber | |
| 2007/0043414 A1 | 2/2007 | Fifer et al. | |
| 2007/0043424 A1 | 2/2007 | Pryor | |
| 2007/0088396 A1 | 4/2007 | Jacobson | |
| 2007/0088418 A1 | 4/2007 | Jacobson | |
| 2007/0150020 A1 | 6/2007 | Hokanson et al. | |
| 2007/0154801 A1 | 7/2007 | Hyung et al. | |
| 2007/0156126 A1 | 7/2007 | Flaherty et al. | |
| 2007/0179552 A1 | 8/2007 | Dennis et al. | |
| 2007/0197939 A1 | 8/2007 | Wallace et al. | |
| 2007/0247786 A1 | 10/2007 | Aamodt et al. | |
| 2007/0255295 A1 | 11/2007 | Starkebaum et al. | |
| 2007/0255383 A1 | 11/2007 | Gerber et al. | |
| 2007/0293909 A1 | 12/2007 | Cowan et al. | |
| 2007/0293922 A1 | 12/2007 | Soltis et al. | |
| 2007/0299492 A1 | 12/2007 | Zhang et al. | |
| 2008/0009750 A1 | 1/2008 | Aeby et al. | |
| 2008/0051704 A1 | 2/2008 | Patel et al. | |
| 2008/0071178 A1 | 3/2008 | Greenland et al. | |
| 2008/0103578 A1 | 5/2008 | Gerber | |
| 2008/0132981 A1 | 6/2008 | Gerber | |
| 2008/0132982 A1 | 6/2008 | Gerber | |
| 2008/0148554 A1 | 6/2008 | Merrill et al. | |
| 2008/0172118 A1 | 7/2008 | Johnson et al. | |
| 2008/0275350 A1 | 11/2008 | Liao et al. | |
| 2008/0283066 A1 | 11/2008 | Delgado et al. | |
| 2009/0163969 A1 | 6/2009 | Donofrio | |
| 2009/0177095 A1 | 7/2009 | Aeby et al. | |
| 2009/0192514 A1 | 7/2009 | Feinberg et al. | |
| 2009/0192585 A1 | 7/2009 | Bloom et al. | |
| 2009/0234367 A1 | 9/2009 | Verma | |
| 2009/0270741 A1 | 10/2009 | Vanney et al. | |
| 2009/0275818 A1 | 11/2009 | Rau et al. | |
| 2009/0299429 A1 | 12/2009 | Mayotte | |
| 2009/0326346 A1 | 12/2009 | Kracker et al. | |
| 2010/0030063 A1 | 2/2010 | Lee et al. | |
| 2010/0063478 A1 | 3/2010 | Selkee | |
| 2010/0082087 A1 | 4/2010 | Silipo et al. | |
| 2010/0179561 A1 | 7/2010 | Pilarski et al. | |
| 2010/0304209 A1 | 12/2010 | Lund et al. | |
| 2010/0305653 A1 | 12/2010 | Lund et al. | |
| 2011/0190842 A1 | 8/2011 | Johnson et al. | |

FOREIGN PATENT DOCUMENTS

| WO | 2009120636 A1 | 10/2009 |
|----|---------------|---------|
| WO | 2009124287 A1 | 10/2009 |

OTHER PUBLICATIONS

Notification of Transmittal of the International Preliminary Report on Patentability dated Jul. 25, 2008 for corresponding PCT Application No. PCT/US2007/001886, (8 pgs.).

Office Action for U.S. Appl. No. 11/606,774, dated Jul. 10, 2009, 11 pages.

Response to Office Action for U.S. Appl. No. 11/606,774, filed Sep. 10, 2009, 8 pages.

Office Action for U.S. Appl. No. 11/606,626, dated Jul. 8, 2009, 14 pages.

Response to Office Action for U.S. Appl. No. 11/606,626, filed Sep. 1, 2009, 8 pages.

Office Action from U.S. Appl. No. 11/606,774, dated Sep. 19, 2012, 18 pp.

Final office action for U.S. Appl. No. 11/606,774, mailed Oct. 27, 2010, 15 pages.

Response to final office action for U.S. Appl. No. 11/606,774, filed on Dec. 21, 2010, 14 pages.

Office Action from U.S. Appl. No. 11/606,774, dated Mar. 29, 2011, 19 pp.

Response to Office Action dated Mar. 29, 2011, from U.S. Appl. No. 11/606,774, filed Jun. 29, 2011, 18 pp.

Office Action from U.S. Appl. No. 11/606,626, dated Dec. 16, 2009, 9 pp.

Response to Office Action dated Dec. 16, 2009, from U.S. Appl. No. 11/606,626, filed Mar. 16, 2010, 14 pp.

Final office action for U.S. Appl. No. 11/606,774, dated Oct 12, 2011, 14 pages.

Response to final action for U.S. Appl. No. 11/606,774, filed Dec. 9, 2011, 16 pages.

Office Action from U.S. Appl. No. 11/606,774, dated Jan. 7, 2010, 14 pp.

Response to Office Action dated Jan. 7, 2010, from U.S. Appl. No. 11/606,774, filed Apr. 7, 2010, 17 pp.

U.S. Appl. No. 13/096,881, filed Apr. 28, 2011, entitled "Implantable Medical Device Fixation" by Vladimir Grubac.

U.S. Appl. No. 13/074,948, filed Mar. 29, 2011 entitled "Implantable Medical Device Fixation Testng "by Nathan T. Lee.

U.S. Appl. No. 13/284,761, filed Oct. 28, 2011 entitled "Implantable Medical Device Fixation Testing "by Thomas A. Anderson.

Medtronic, Inc., "Cardiac Resynchronization Therapy for Heart Failure Management—Implant and Follow-up—Brief Overview" 4 pages (2002).

Luna Technologies, "About Distributed Sensing Technology" 2 pages (2010).

Response to Office Action for U.S. Appl. No. 11/606,774, dated Dec. 19, 2012, 17 pp.

\* cited by examiner

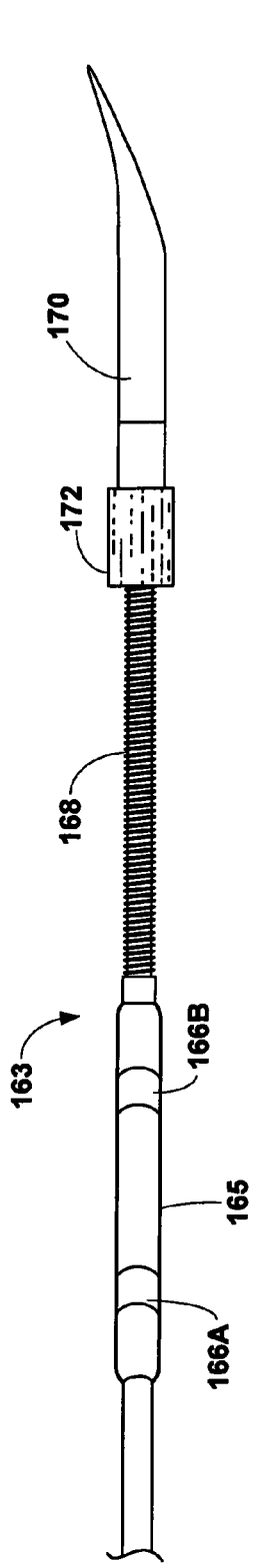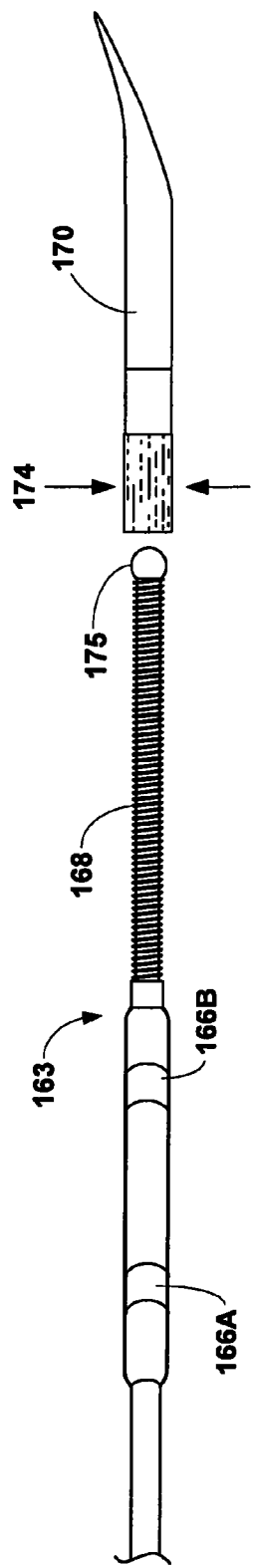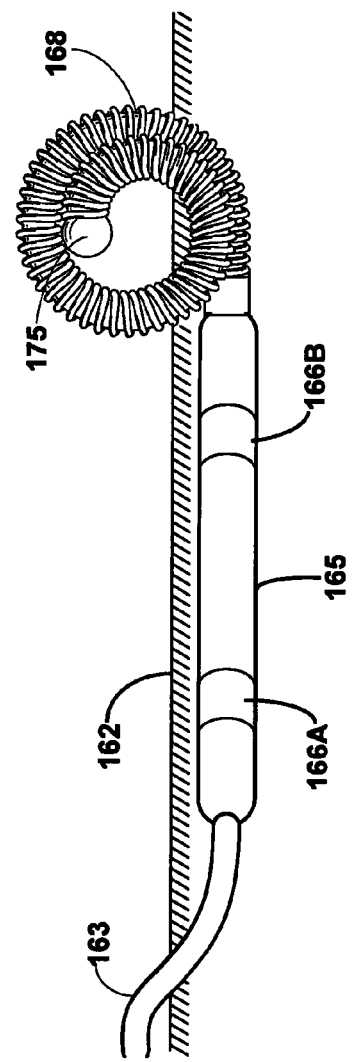
FIG. 5A
FIG. 5B
FIG. 5C

SUTURELESS IMPLANTABLE MEDICAL DEVICE FIXATION

TECHNICAL FIELD

The invention relates to implantable medical devices and, more particularly, to techniques for fixation of implantable medical devices within the body of a patient.

BACKGROUND

Medical devices such as electrical stimulators, leads, and electrodes are implanted to deliver therapy to one or more target sites within the body of a patient. To ensure reliable electrical contact between the electrodes and the target site, fixation of the device, lead, or electrodes is desirable. Minimally invasive surgery, such as laparoscopy, permits device implantation with less pain and recovery time than open surgery. However, minimally invasive surgery tends to be more complicated than open surgery. For example, forming a suture for device fixation requires a surgeon to manipulate instruments within the confines of cannulas and, while watching remotely though a viewing instrument, pass a needle through tissue and tie a knot. Because of this complexity, forming a single suture for fixation of an implantable medical device may take several minutes. Operative duration is a contributing factor in morbidity. Consequently, reducing surgical time and complexity is highly desirable.

SUMMARY

In general, the invention is directed to techniques for sutureless fixation of an implantable medical device, such as an electrical stimulator, lead, or electrode. The techniques make use of an actively deployable fixation clip that can be integrated with the implantable medical device. The actively deployable fixation clip may be formed from an elastic material or shape memory material, and is operable to fixate the implantable medical device within or against body tissue. Upon deployment, the fixation clip initiates a shape change that causes the clip to assume a shape that provides fixation of the implantable medical device.

As an example, the implantable medical device may be an electrical stimulation lead with an actively deployable fixation clip attached to a distal end of the lead. Upon passage of the distal end of the lead through body tissue, the fixation clip is deployed to prevent withdrawal of the lead from the body tissue. In some embodiments, the clip may be deployed when the distal end of the lead exits the tissue, thereby fixing a portion of the lead within the body tissue. The clip may be deployed in a variety of ways, such as releasing the clip from a restraint so that the clip can assume a different shape or otherwise activating the shape change capabilities of the clip.

In some embodiments, an actively deployable clip may be attached to different portions of a lead, such as a portion of the lead adjacent to a tissue surface on an entry side of the body tissue. Further, in some embodiments, an electrical stimulation lead may include multiple actively deployable clips disposed at different positions along the lead. For example, a first fixation clip may be deployed at an entry point of a lead into a tissue site, and a second fixation clip may be deployed at an exit point of the lead from the tissue site, providing robust fixation of the lead at two or more points within the body tissue.

As an illustration, one or more fixation clips may be deployed on a gastric stimulation lead, e.g., on one or both sides of one or more electrodes that are carried by the lead and embedded with the muscle wall of the stomach. The gastric stimulation lead may include a releasably attached needle that penetrates the muscle wall at an entry point and then extends out of the muscle wall via an exit point. A fixation clip may be positioned at the distal end of the lead for deployment outside the muscle wall just beyond the exit point, thereby fixating the electrodes or electrodes carried by the lead within the muscle wall. In some embodiments, another fixation clip may be provided on the lead body for deployment just outside the entry point of the lead. In this manner, the lead is anchored at two points to resist axial movement in either direction.

In one embodiment, the invention is directed to a device comprising a medical implant and an actively deployable clip attached to the medical implant. The actively deployable clip operates to restrict movement of the medical implant once the actively deployable clip is deployed within a body of a patient.

In another embodiment, the invention is directed to a method comprising implanting a device. The device includes a medical implant, and an actively deployable clip attached to the medical implant. The method further includes deploying the actively deployable clip to restrict movement of the medical implant once the actively deployable clip is deployed within a body of a patient.

Embodiments of the invention may provide one or more of the following advantages. For example, embodiments of the invention may eliminate the need to form sutures for fixation, thereby reducing surgical time, which may correlate to a reduction in morbidity. Furthermore, embodiments of the invention may facilitate minimally invasive surgery by reducing surgical complexity, promoting a reduction in surgical errors. By reducing the time and difficulty of fixation techniques, more robust fixation for implantable medical devices may result. For example, surgeons may be more inclined to add fixation points if the procedure is less difficult and time-consuming.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 5A-5C are illustrations of an assembly including an electrical stimulation lead with an actively deployable clip and a releasably attached needle used to insert the electrical stimulation lead within a body.

DETAILED DESCRIPTION

Figure 1:
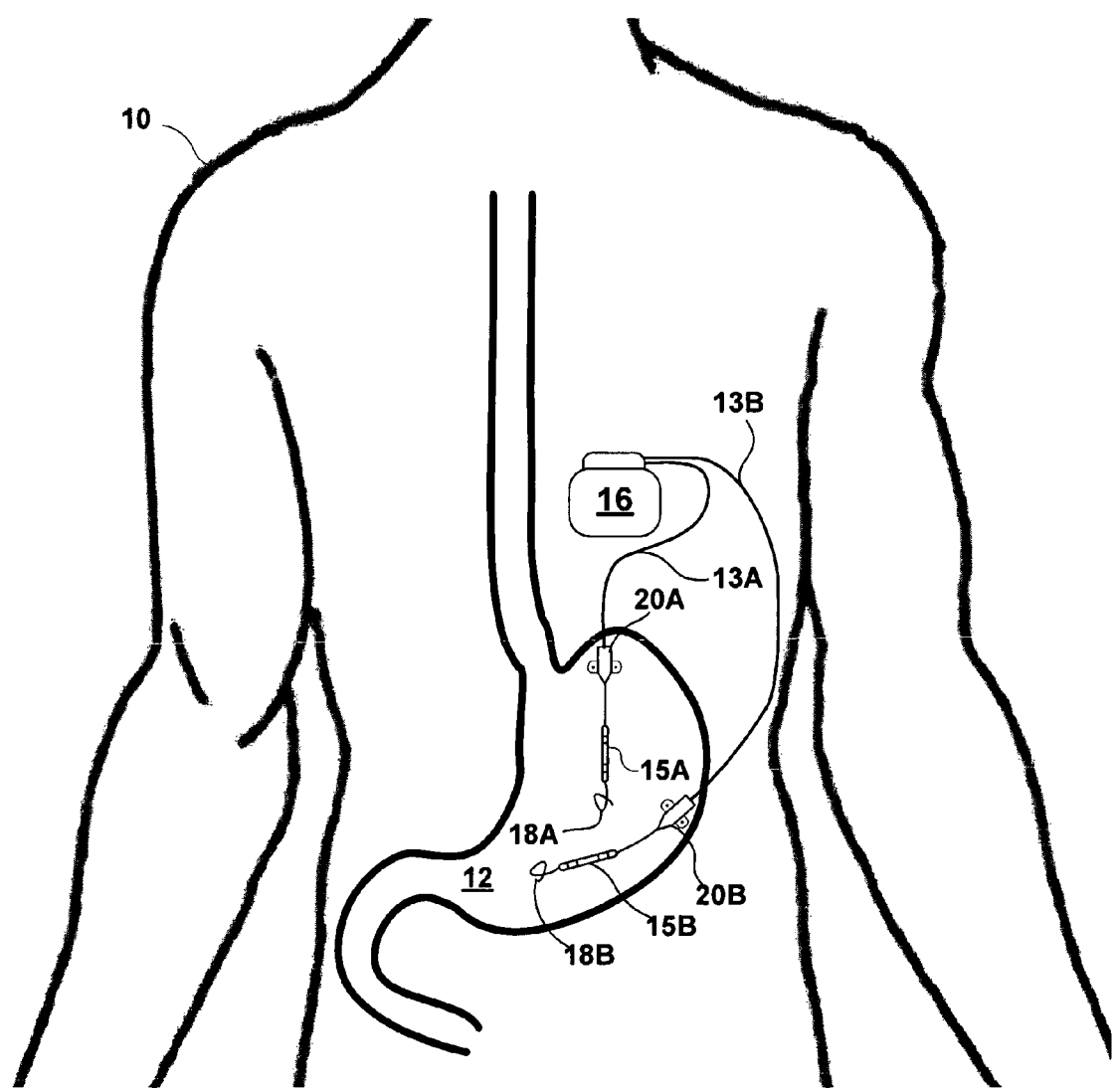
FIG. 1 is an illustration of a torso of a patient having an implantable medical implant including electrical stimulation leads with actively deployable clips.

FIG. 1 is an illustration of a torso of patient 10, in which stomach 12 is visible. Although various embodiments of the invention may be useful for fixation of a variety of implantable medical devices, fixation of implantable medical leads carrying electrodes for gastric stimulation will be described for purposes of illustration. In the example of FIG. 1, an implantable electrical stimulation generator 16 provides electric stimulation to patient 10, e.g., in the form of stimulation pulses, via stimulation electrodes carried in an electrode section 15A, 15B of one or more electrical stimulation leads 13A, 13B.

Stimulation generator 16 may be used to electrically stimulate gastrointestinal tract via one or more stimulation electrodes in an electrode section 15A, 15B. One or more electrodes may be integrated with stimulation generator 16, or carried by leads 13A, 13B electrically coupled to the stimulation generator. Stimulation generator 16 may be positioned subcutaneously in the abdominal wall, for example, such as in the right mid quadrant. Stimulation generator 16 may be anchored within a subcutaneous pocket using sutures or, in other embodiments, with actively deployable clips. In some cases, stimulation generator 16 may be held in place by body tissue within patient 10.

For gastric stimulation, the electrical stimulation may have parameters selected to be effective in inducing a sensation of satiety or nausea, or promoting gastric motility. More particularly, the electrical stimulation parameters may be selected to treat obesity, alleviate gastroparesis, or address other gastrointestinal disorders. For stimulation of other organ or tissue sites, the stimulation parameters may be selected to be effective in addressing applicable disorders. For example, stimulation generator 16, leads 13A, 13B and electrode section 15A, 15B may be configured for delivery of stimulation therapy to patients to treat a variety of symptoms or conditions such as chronic pain, tremor, Parkinson's disease, epilepsy, neuralgia, urinary or fecal incontinence, or sexual dysfunction. The stimulation parameters may include electrode combination, electrode polarity, current or voltage amplitude, pulse width and pulse rate.

In the example of FIG. 1, one or more stimulation electrodes in electrode section 15A, 15B are placed in the muscle wall of stomach 12 using standard surgical procedures such as laparotomy or laparoscopy. Stimulation electrode section 15A, 15B may be positioned anywhere in stomach 12, but typically will be placed along either the greater curvature or lesser curvature to induce symptoms of gastroparesis. Stimulation leads 13A, 13B may be fixed relative to stomach 12 via anchors 20A, 20B and actively deployable clips 18A, 18B. Clips 18A, 18B may be formed from elastic or shape memory materials. Anchors 20A, 20B and actively deployable clips 18A, 18b are attached to leads 13A, 13B, respectively, adjacent stimulation electrode section 15A, 15B, respectively. Anchors 20A, 20B may be attached to the tissue of patient 10 using sutures or actively deployable clips.

Actively deployable clips 18A, 18B may be deployed by releasing the clips from respective retainer mechanisms, as will be described. For example, a retainer wrap, band or binder may be cut or broken to release a clip 18A, 18B. In some cases, the retainer mechanism may be broken by squeezing it, e.g., with a forceps. Deployment of an actively deployable clip 18A, 18B by releasing it from retainer mechanism permits the clip to initiate a shape change due to general elasticity or shape memory properties. For example, the clip 18A, 18B may change from a substantially straight or slightly curved shape, prior to deployment, to a moderately or highly curved or spiral shape, following deployment, as shown in FIG. 1. The post-deployment shape of clip 18A, 18B may be a regular or irregular shape, provided that the clip assumes a shape that interacts with body tissue to resist movement of lead 13A, 13B.

Stimulation electrode section 15A, 15B may include one or more intramuscular electrodes and/or surface electrodes. Intramuscular electrodes are placed in the muscle wall of the stomach, preferably in the circular muscle layer. These stimulation electrodes may be inserted either from inside of the stomach or from outside the stomach. Surface electrodes may be attached to, for example, the serosa or the mucosa. In either case, actively deployable clips 18A, 18B operate to restrict movement of stimulation leads 13A, 13B once the actively deployable clips are deployed so that electrode section 15 maintains electrical contact with stomach 12.

Actively deployable clips 18A, 18B can be deployed with greater ease and in less time than equivalently functional sutures. Consequently, actively deployable clips 18A, 18B can reduce surgical time for implantation of a gastric stimulation system as shown in FIG. 1. In other embodiments, actively deployable clips 18A, 18B may be used with other implantable medical devices such as electrical stimulation leads for cardiac stimulation or neurostimulation, cardiac stimulation or neurostimulation generators, drug delivery pumps, or the like, to reduce surgical time and complexity involved in fixation.

Figure 2:
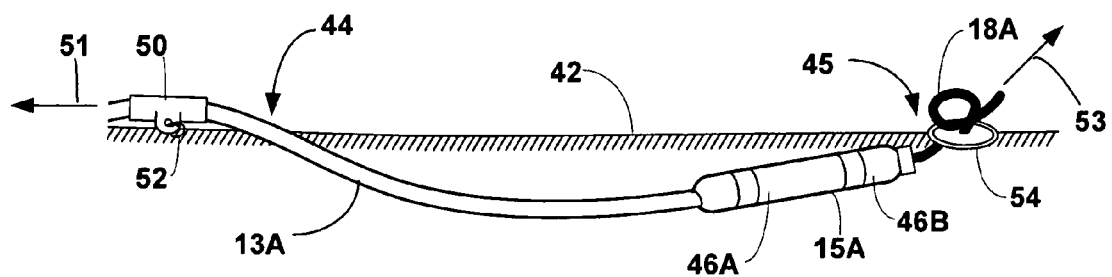
FIG. 2 is an illustration of an implanted electrical stimulation lead with an actively deployable clip secured to an anchor disk within the body of a patient.

FIG. 2 is an illustration of electrical stimulation lead 13A with an actively deployable clip 18A secured to an anchor disk 54 through tissue 42 within the body of a patient 10. For a gastric stimulation application, tissue 42 may be muscle tissue in the wall of stomach 12. Electrical stimulation lead 13A may be one of the electrical stimulation leads in FIG. 1. Electrical stimulation lead 13A includes electrical stimulation electrode section 15A. In the example of FIG. 2, electrode section 15 carries two electrodes 46A, 46B. Electrical stimulation electrode section 15A may be positioned adjacent to a distal end of electrical stimulation lead 13A. The electrodes 46A, 46B in electrical stimulation electrode section 15A are coupled to stimulation generator via conductors within lead 13A.

Actively deployable clip 18A is attached to the distal end of electrical stimulation lead 13A and operates to restrict movement of the electrical stimulation lead relative to tissue 42. Actively deployable clip 18A is deployed by a surgeon after inserting electrical stimulation lead 13A through tissue 42 and then through a distal anchor disk 54. For example, electrical stimulation lead 13A and actively deployable clip 18A may be part of an assembly including a releasably attached needle that guides actively deployable clip 18A and electrical stimulation lead 13A through tissue 42. A surgeon urges lead 13A into tissue 42 at entry point 44 and extends the lead through the tissue so that a distal end of the lead exits the tissue at exit point 45.

Upon protrusion of the distal end of lead 13A from exit point 45, an aperture of the annular anchor disk 54 may be placed over the distal end to a point that is on a proximal side of the clip 18A. Upon deployment of clip 18A, the clip expands under elastic or shape memory forces and is captured by anchor disk 54, so that lead 13A resists movement into tissue 42 via the exit point 45. In particular, the diameter of anchor disk 54 is larger than the opening created by exit point 45. As a result, anchor disk 54 bears against tissue at exit point 45. In turn, clip 18A has a size larger than the aperture of anchor disk 54, and bears against the surface of the disk, thereby resisting inward movement of lead 13A.

In other cases, actively deployable clip 18A can be used without an anchor disk 54 to fixate the distal end of electrical stimulation lead 13A relative to tissue 42. Instead, upon deployment, elastic or shape memory forces cause clip 18A to expand to a size that is larger than the opening created by exit point 45. In this manner, clip 18A bears against the outer surface of tissue 42 to resist inward movement of lead 13A. In particular, lead 13A cannot be pulled back through entry point 44 in a proximal direction, indicated by arrow 51, providing fixation of the lead to resist axial movement in at least one direction.

A proximal anchor 50 also may be attached to electrical stimulation lead 13A. Anchor 50 is fixated to tissue 42 with suture 52. In the example of FIG. 2, anchor 50 may take the form of a cylindrical collar that extends about at least a portion of lead 13A. The collar-like anchor 50 may include one or more wing-like elements that extend outward from lead 13A and include an aperture to receive a suture. Before or after deployment of clip 18A at the distal end of lead 13A, but after insertion of the lead into tissue 42, proximal anchor 50 is sutured to an outer surface of tissue 42 at a point near tissue entry point 44.

Proximal anchor 50 resists movement of lead 13A in a distal direction, indicated by arrow 53. In other words, proximal anchor 50 and suture 52 resist withdrawal of lead 13A from exit point 45. In addition, proximal anchor 50 and suture 52 may resist withdrawal of lead 13A from entry point 44. Hence, proximal anchor 50 and deployable clip 18A resist axial movement of lead 13A in two directions, i.e., distal movement out of exit point 45 in a distal direction 53 and proximal movement out of entry point 44 in a proximal direction 51. In this manner, electrode section 15A remains firmly implanted within tissue 42 to ensure reliable electrical contact of electrodes 46A, 46B with stomach 12.

For example, if tissue 42 is a muscle such as a stomach muscle, anchor 50 may prevent electrical stimulation lead 13A from being displaced within the patient during muscle contractions. Without anchor 50, a portion of electrical stimulation lead 43 may slide into and/or out of tissue 42. This is undesirable because such movement may displace electrodes 46A, 46B, cause the patient discomfort or added stress on actively deployable clip 18A. In other embodiments, suture 52 may be replaced by an actively deployable clip. In this case, deployable clips may be used in stimulation lead 13A at proximal and distal sides of electrode section 15A.

Actively deployable clip 18A may include an elastically deformable material wire that changes shape, e.g., from a substantially straight or slightly curved shape to a moderately or highly curved shape. In the example of FIG. 2, once clip 18A is released from a retainer mechanism, such as a wrap or binder, the clip assumes a spiral shape. The spiral shape increases the size of clip 18A in terms of the ability of the clip to interfere with tissue 42 when lead 13A is pulled inward relative to exit point 45. In some embodiments, the elastically deformable material wire used to form deployable clip 18A may be a shape memory metal, such as Nitinol. Other biocompatible materials such as stainless steel, titanium or biocompatible polymeric materials may be used to form clip 18A.

An exemplary implantation procedure for electrical stimulation lead 13A is described as follows. A surgeon implants electrical stimulation lead 13A by pushing or pulling actively deployable clip 18A through tissue 42. For example, a needle may be releasably attached to actively deployable clip 18A to punch through tissue 42 in front of actively deployable clip 18A. The surgeon then pulls actively deployable clip 18A though a central aperture of annular anchor disk 54, which is just beyond the surface of tissue 42. Again a needle may be used to lead actively deployable clip 18A through anchor disk 54.

Then, the surgeon deploys actively deployable clip 18A on the distal side of anchor disk 54 relative to electrical stimulation electrode section 15A. Once deployed, actively deployable clip 48 changes from a substantially straight or slightly curved shape to assume the spiral configuration shown in FIG. 2. Again, clip 18A may be deployed by disengaging a retainer mechanism. For example, a wrap or binder that extends about clip 18A to hold it in its unexpanded position may be severed, cut, squeezed or crushed using any of a variety of surgical tools to permit the clip to deploy. Once actively deployable clip 18A is deployed to fixate the distal end of electrical stimulation lead 13A just outside exit point 45, the surgeon may secure proximal anchor 50 to an outer portion of tissue 42 by tying a knot in suture 52 at a point proximate to entry point 44.

After securing electrical stimulation lead 13A with actively deployable clip 18A, distal anchor 54, and proximal anchor 50, the surgeon may connect the proximate end of electrical stimulation lead 13A to a stimulation generator. Various modifications to the described techniques of implantation of electrical stimulation lead 43 can be made. For example, anchor 50 may be attached with suture 52 prior to deploying actively deployable clip 18A. As another example, actively deployable clip 18A may be used without anchor disk 54. As a further alternative, actively deployable clips may be used at both the entry point 44 and exit point 45, eliminating the need to suture proximal anchor 50. In either case, electrode section 15A is retained within tissue 42 to ensure reliable electrical contact.

Figure 3:
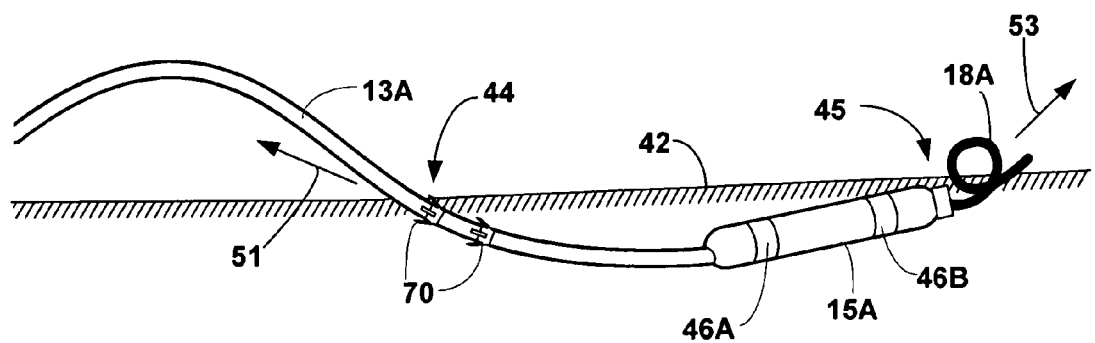
FIG. 3 is an illustration of an implanted electrical stimulation lead with an actively deployable clip and tines to secure the implanted electrical stimulation lead within the body of a patient.

FIG. 3 is an illustration of electrical stimulation lead 13A with actively deployable clip 18A secured to tissue 42 within the body of a patient. The embodiment shown in FIG. 3 is substantially similar to the embodiment shown in FIG. 2. In the example of FIG. 3, however, actively deployable clip 18A is used for distal fixation of lead 13A without a distal anchor disk 54. In addition, FIG. 3 illustrates the optional use of tine 70 for proximal fixation instead of a proximal anchor 50. Electrical stimulation lead 13A includes electrical stimulation electrodes 46A, 46B within electrode section 15A. Electrode section 15A is adjacent to a distal end of electrical stimulation lead 13A. Stimulation electrodes 46A, 46B are coupled to a stimulation generator via conductors within lead 13A.

Actively deployable clip 18A is attached to the distal end of electrical stimulation lead 13A and operates to restrict movement of electrical stimulation lead 13A. A surgeon deploys actively deployable clip 18A after inserting electrical stimulation lead 13A through tissue 42. For example, electrical stimulation lead 13A and actively deployable clip 18A may be part of an assembly including a releasably attached needle to guide actively deployable clip 18A and electrical stimulation lead 13A through tissue 42. Tines 70 also function to fixate electrical stimulation lead 13A to tissue 42, but are passive in that they do not need to be deployed by the surgeon to restrict movement of electrical stimulation lead 13A. As in the example of FIG. 2, actively deployable clip 18A may include an elastically deformable material wire that changes shape from a substantially straight shape to the spiral shape shown in FIG. 3 when actively deployable clip 18A is deployed.

In the example of FIG. 3, electrical stimulation lead 13A may be implanted in substantially the same manner as electrical stimulation lead 13A of FIG. 2. One difference in the implantation of electrical stimulation lead 13A in FIG. 3 relative to the implantation contemplated in FIG. 2 is that actively deployable clip 18A does not need to be pushed through an anchor disk before being deployed. Instead, once clip 18A clears exit point 45 of tissue 42, it may be actively deployed by a surgeon, e.g., by removing a retainer mechanism, and permitting the clip to expand. However, actively deployable clip 18A could also be used in conjunction with an anchor disk.

Another difference in the implantation of electrical stimulation lead 13A in FIG. 3 is that tines 70 fixate to tissue 70 automatically by virtue of their shape and orientation on the body of the lead. In particular, tines 70 may extend laterally outward from lead 13A. Each tine 70 defines an acute angle relative to the longitudinal axis of lead 13A. The acute angle is on a proximal side of the tines 70, such that the tines ramp or taper from a smaller diameter to a larger diameter as lead 13A is inserted into tissue 42.

If lead 13A is pulled in a proximal direction 51, tines tend to resist movement. In particular, the larger diameter extension of tines 70 interfere with tissue 42, and may bite into the tissue to resists axial movement in the proximal direction 51. In some embodiments, tines 70 may be flexible and elastic, such that they fold inward upon insertion of lead 13A into tissue 42, and expand outward or exert an outward force upon reaching a stable position within the tissue. In either case, tines 70 resist movement of lead 13A in a proximal direction 51.

With tines 70 resisting movement in proximal direction 51, it may be desirable to provide a proximal anchor to resist movement in distal direction 53. However, the spiral wire arrangement provided by clip 18A may bite into tissue 42 to resist movement in distal direction 53 as well as proximal direction 51. Notably, neither tines 70 nor clip 18A require the tying of suture knots to achieve fixation of lead 13A. In this manner, implantation of electrical stimulation lead 13A in the example of FIG. 3 may be less complex and take less time than implantation of a lead with sutured anchors.

Figure 4A:
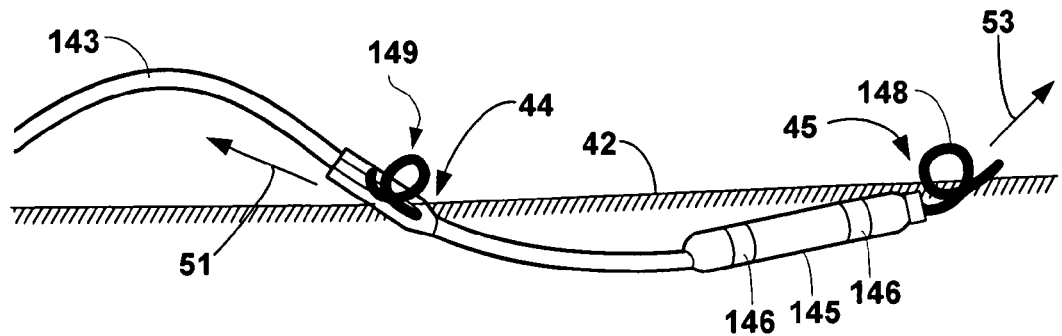
FIGS. 4A-4C are illustrations of an electrical stimulation lead with two actively deployable clips.
Figure 4B:
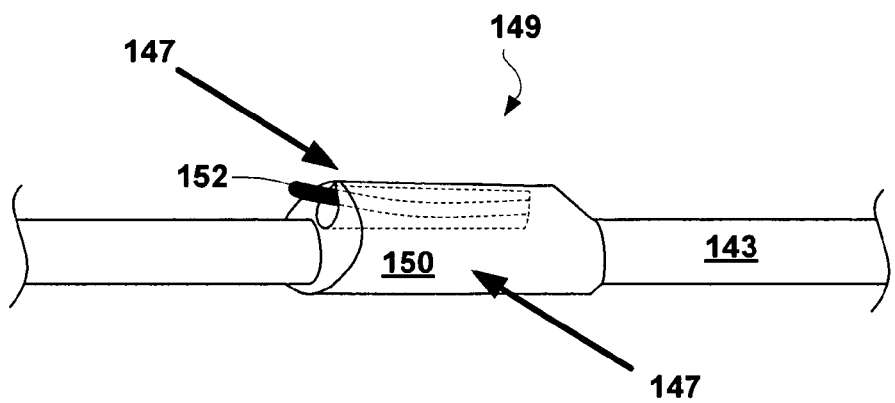
Figure 4C:
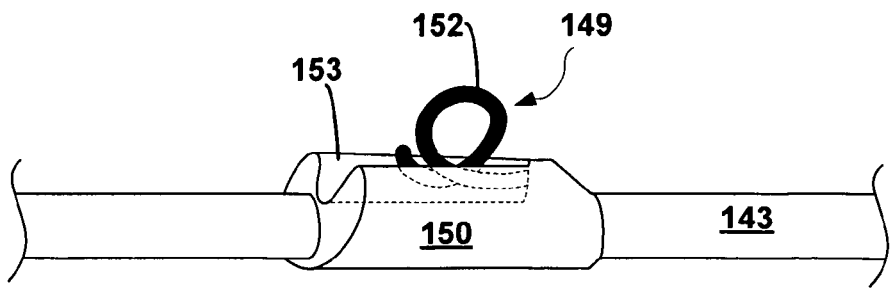

FIGS. 4A-4C are illustrations of an electrical stimulation lead 143 with two actively deployable clips 148 and 149. Electrical stimulation lead 143 includes electrical stimulation electrode section 145, which includes electrodes 146A, 146B. The embodiment shown in FIGS. 4A-4C is substantially similar to the embodiment shown in FIG. 3 except that actively deployable clip 149 provided, and tines 70 are omitted.

In the example of FIG. 4A, a surgeon deploys actively deployable clips 148 and 149 after inserting electrical stimulation lead 143 through tissue 42, e.g., using a releasably attached needle at the distal end of the lead. Actively deployable clip 148 is attached to the distal end of electrical stimulation lead 143 and operates to restrict movement of electrical stimulation lead 143 in a proximal direction 51. Similarly, actively deployable clip 149 also operates to restrict movement of electrical stimulation lead 143, but in a distal direction 53. Actively deployable clip 149 is attached at a more proximate location of electrical stimulation lead 143 than stimulation electrode section 145, and is positioned to be deployed just outside entry point 44 in tissue 42.

Elastically deformable component 152 of actively deployable clip 149 changes shape from a substantially straight shape as shown in FIG. 4B to the spiral shape shown in FIG. 4C when deployed. For example, the elastically deformable component 152 may include a shape memory metal, such as Nitinol. As shown in FIG. 4B, actively deployable clip 149 includes a thin-walled clip retainer 150, which holds elastically deformable component 152 in a retracted position to allow positioning of electrical stimulation lead 143.

Once a surgeon positions electrical stimulation lead 143 as desired within tissue 42, the surgeon actively deploys a clip 149. For example, the surgeon actively deploys actively deployable clip 149 by compressing clip retainer 150, as indicated by arrows 147 to break the thin-walled clip retainer. For example, thin-walled clip retainer 150 may consist of a polymer that tears, breaks or ruptures when compressed. Alternative materials for retainer 150 may include paper, plastic, thin metals, or biosorbable materials. When retainer 150 ruptures, as shown in FIG. 4C, it creates an opening 153 that releases elastically deformable component 152 from its retracted position as shown in FIG. 4B. Once released, elastically deformable component 152 expands to assume a substantially relaxed state in the spiral configuration as shown in FIGS. 4A and 4C.

Various modifications can be made to the embodiment shown in FIGS. 4A-4C. For example, thin-walled clip retainer 150 may be replaced within another retainer mechanism to hold elastically deformable component 152 in a retracted position. For example, a slideable ring, a latch, binder, band, or other mechanism may be used in place of thin-walled clip retainer 150. Furthermore, clip retainer 150 or a variation thereof can be readily adapted to implantable medical devices other than electrical stimulation leads, such as catheters, stimulation generators, drug delivery pumps, or the like.

FIGS. 5A-5C are illustrations of a lead assembly 160, which includes electrical stimulation lead 163 with actively deployable clip 168 and needle 170. For example, electrical stimulation lead 163 may be substantially the same as electrical stimulation leads 13A or 13B in FIG. 1, electrical stimulation lead 13A in FIG. 2, electrical stimulation lead 13A in FIG. 3 and/or electrical stimulation lead 143 in FIGS. 4A-4C. Needle 170 allows electrical stimulation lead 163 and actively deployable clip 168 to be forcibly inserted through body tissue 162 and, optionally, an anchor disk.

Needle 170 is releasably attached to actively deployable clip 168 and electrical stimulation lead 163 with clip retainer 172. Clip retainer 172 has dual functions of releasably attaching needle 170 to lead 163, and constraining actively deployable clip 168 in an undeployed position. In other embodiments, these functions may be performed by separate components.

Compressing clip retainer 172, e.g., in direction 174 as shown in FIG. 5B, deploys actively deployable clip 168 from the open position and allows it to assume a relaxed spiral closed position to fixate electrical stimulation lead 163 to tissue 162 as shown in FIG. 5C. Compressing clip retainer 172 also releases needle 170 from actively deployable clip 168 and electrical stimulation lead 163. Clip retainer 172 may be glued, crimped, bonded or otherwise attached to a proximal end of needle 170. Upon deployment of clip 168, the surgeon withdraws needle 170 and clip retainer 172 from the patient via a laparoscopic port.

In one embodiment, clip retainer 172 operates by holding enlarged end portion 175 within clip retainer 172 with a plurality of indented cable strands. In some embodiments, enlarged end portion 175 may be generally spherical or hemispherical in shape and may be ball-like. Clip retainer 172 may include a generally cylindrical recess to receive enlarged end portion 175 of clip 168. Compressing clip retainer 172 misaligns the indents, which cooperate to hold enlarged end portion 175 within retainer 172. In other embodiments, clip retainer 172 may be cut or broken to release enlarged end portion 175 of clip 168.

In further embodiments, enlarged end portion 175 may be held within clip retainer 174 by friction fit, snap fit or adhesive bonding, such that end portion 175 can be withdrawn from retainer 174 by pulling needle 170 away from the clip 168 with sufficient force. Hence, when needle 170 and lead 163 are pushed into the tissue, the connection between retainer 174 and clip 168 remains intact. When a pulling force is exerted on needle 170 in a distal direction away from exit point, however, retainer 174 disengages from end portion 175 of clip 168, permitting deployment of the clip. To facilitate separation of clip 168 from clip retainer 174, opposite pulling forces may be exerted on both ends of lead 163, i.e., on needle 170 in a distal direction and on a portion of lead 163 outside of the tissue entry point in a proximal direction.

The structure and operation of actively deployable clip 168 and clip retainer 172 may be similar to the structure and operation of similar devices described in U.S. Pat. No. 6,514,265 to Ho et al., titled "TISSUE CONNECTOR APPARATUS WITH CABLE RELEASE," the entire content of which is incorporated herein by reference. One difference between the embodiments shown in U.S. Pat. No. 6,514,265 and actively deployable clip 168 is that actively deployable clip 168 assumes a substantially straight or slightly curved shape while in an open position, rather than the more drastically curved shape shown in U.S. Pat. No. 6,514,265. This is to facilitate threading electrical stimulation lead 163 through tissue within the patient. Other actively deployable clip designs that may be readily adapted to provide sutureless fixation of an implantable medical device are described in, for example, U.S. Pat. No. 6,926,730 to Nguyen, et al., titled "MINIMALLY INVASIVE VALVE REPAIR PROCEDURE AND APPARATUS" and U.S. Pat. No. 6,913,607 to Ainsworth, et al., titled "SELF-CLOSING SURGICAL ACTIVELY DEPLOYABLE CLIP FOR TISSUE."

In operation, needle 170 is inserted into tissue and use to place an electrode section 165 of lead 163 within the tissue, e.g., such as a muscle layer of the stomach wall. Electrode section 165 includes one or more electrodes 166A, 166B. Needle 170 enters the tissue through an entry point and is then threaded through the tissue and exits through an exit point. Upon forcing the needle 170 out of the exit point in the tissue, the surgeon continues to move the lead 163 forward until at least a portion of the straight, undeployed clip 168 extends outside of the exit point.

The surgeon then deploys the clip 168, e.g., by squeezing clip retainer 172. When clip 168 is released from clip retainer 172, the clip assumes a spiral-like shape having a size and shape that interferes with the outer surface of the tissue and resists movement of lead 163 in a proximal direction, i.e., resists pulling back into the opening defined by exit point. As in the example of FIGS. 4A, 4B, 4C, a proximal clip or proximal anchor also may be provided. In general, clip 168 resists movement of lead 163 in a proximal direction, and thereby ensures reliable electrical contact between electrodes 166A, 166B and tissue in the stomach wall of the patient.

Figure 6A:
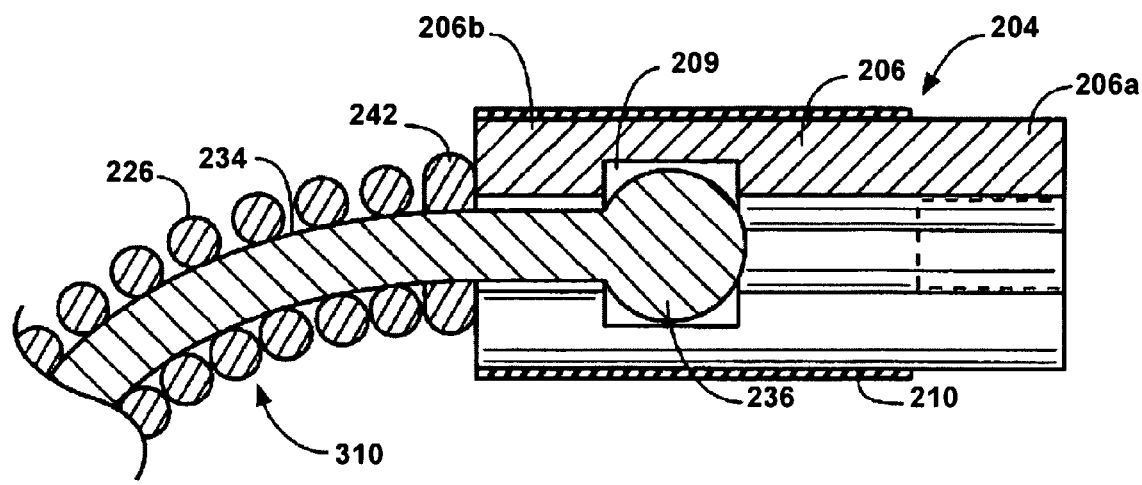
FIGS. 6A-6D illustrate an actively deployable clip and clip retainer and show techniques for releasing the clip retainer.
Figure 6B:
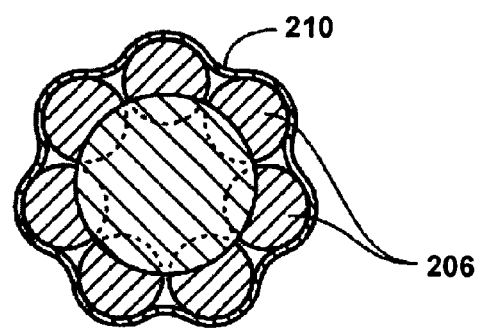
Figure 6C:
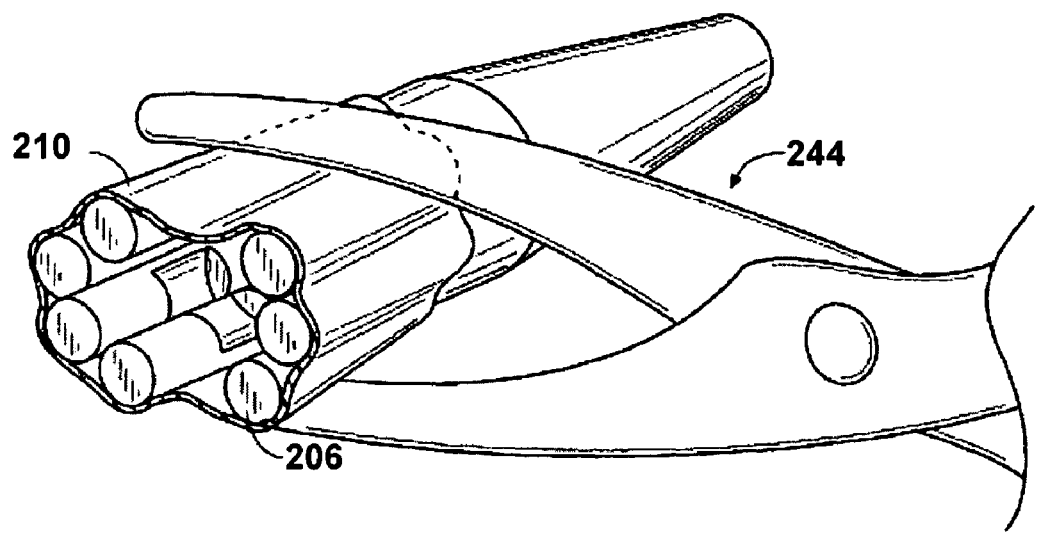
Figure 6D:
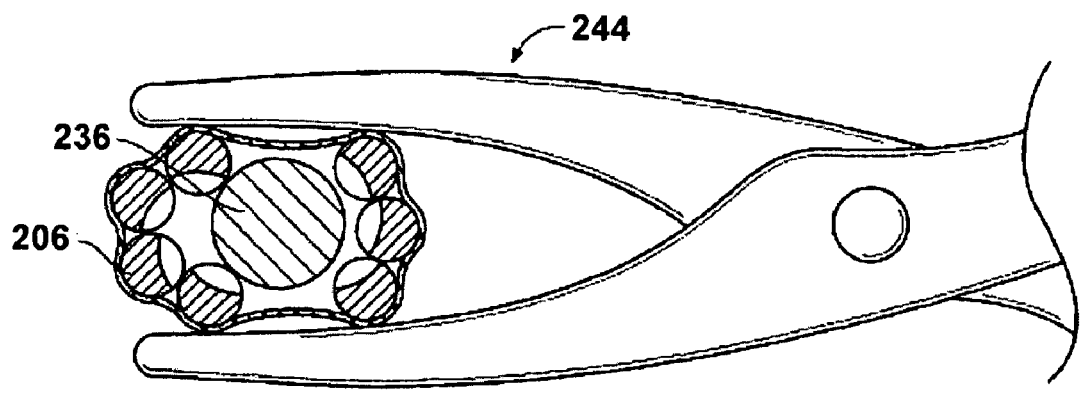

FIGS. 6A-6D illustrate close-up views of actively deployable clip 310 and clip retainer 204. Specifically, FIG. 6A is a cross-sectional side view of actively deployable clip 310 and clip retainer 204. FIG. 6B is a cross-sectional end view of the clip retainer 204. FIG. 6C is a perspective view of the clip retainer 204 during compression of clip retainer 204 to release actively deployable clip 310, and FIG. 6D is an end view of the clip retainer 204 during compression of clip retainer 204 to release actively deployable clip 310. For example, actively deployable clip 310 may be the same as actively deployable clip 168 (FIGS. 5A-5C), and clip retainer 204 may be the same as clip retainer 172 (FIGS. 5A-5B).

Clip retainer 204 includes a plurality of substantially rigid strands 206, arranged substantially parallel to one another and circularly about a longitudinal axis of the aligned strands, to form a tube-like configuration, as can be seen in the cross-section view of FIG. 6B. Strands 206 may be wires, cables or some other substantially rigid strand elements arranged in manner as shown in FIG. 6B.

The distal portions 206b of strands 206 contain notches 209 which are formed into strands 206 to a depth equal to approximately half the diameter of strands 206. When strands 206 are arranged in the circular configuration described above, the notches 209 form a chamber for receiving and holding enlarged ball 236 which is at the proximal end of actively deployable clip 310. In other embodiments, the proximal end of actively deployable clip 310 may have an enlarged barrel shape, or other shape that may be easily grasped and easily released. For example, the notches may be placed about 0.015" from the distal ends of strands 206. However, this distance may be modified to create more or less compression of the spring 226 while actively deployable clip 310 is held by clip retainer 204.

Clip retainer 204 is shown as having seven strands 206. In other embodiments, fewer or more than seven strands may be used. The number of strands may vary depending on, for example, the size of the clip as well as the cross-sectional size of strands 206. Typically, the number of strands may range from two to ten and more particularly may range from five to seven, although other numbers may be used.

Shrink tubing 210, a shrink wrap layer, is provided over at least distal portions 206b of strands 206. Shrink tubing 210 compresses strands 206 to hold them in place against enlarged ball 236. Together, shrink tubing 210 and strands 206 effectively hold the ball 236 captive within the notches 209.

Clip retainer 204 is movable between a locked position (FIGS. 6A-6B) and an unlocked position (FIGS. 6C-6D). In the locked position enlarged ball 236 is held within the notches 209 and consequently, spring 226 is held in a compressed position, thereby maintaining elastically deformable material 234 of actively deployable clip 310 in its deformed or open position. In the unlocked position, the ball 236 is released from the notches, thereby allowing the spring 226 to expand, which causes elastically deformable material 234 to assume an unstressed position and causes actively deployable clip 310 to close.

When elastically deformable material 234 is positioned within the tissue in its undeformed configuration, a residual stress may be useful to securely attach actively deployable clip 310 to tissue. In order for elastically deformable material 234 to retain sufficient compression force in its undeformed configuration, elastically deformable material 234 should not be stressed past its yield point in the open configuration of actively deployable clip 310. In some embodiments, elastically deformable material 234 may be heat activated, or a combination of heat activation and pseudoelastic properties may be used.

The size of actively deployable clip 310 will vary depending on the specific application. For example, the diameter of elastically deformable material 234 may be, for example, between 0.001 and 0.015 inches. For example, the diameter may be between 0.001 and 0.008 inch. In a closed position, actively deployable clip 310 may form a loop with a diameter between 0.0125 and 0.0875 inches. In other embodiments, actively deployable clip 310 may form a loop with a diameter between 0.1 and 0.25 inches or an even larger loop. In embodiments that provide a loop with a diameter between 0.1 and 0.25 inches, the diameter of elastically deformable material 234 may be, for example, between 0.01 and 0.05 inches. In general, the diameter of elastically deformable material 234 may be somewhat proportional to the diameter of a loop formed by actively deployable clip 310 when in the closed position. While elastically deformable material 234 is shown as having a generally circular cross-section, in other embodiments, elastically deformable material 234 and actively deployable clip 310 may have rectangular or other cross-sectional shapes.

Clip retainer 204 is opened by applying a compressive force to the shrink tube 210 and bundle of strands 206, as shown in FIGS. 6C and 6D. Strands 206 are distorted from their circular configuration under the compression. This change in shape stretches the shrink tube 210 from a circular configuration to a somewhat elliptical configuration, and removes some of the notches 209 from contact with the ball 236, as shown in FIG. 6C, thereby permitting removal of the ball 236 from within the chamber previously formed by notches 209 in the closed position.

Advantageously, the compressive force may be applied at any opposing locations around the circumference of the shrink tube as long as the implement applying the force is oriented at an angle to strands 206, preferably substantially perpendicular thereto, to allow the implement to traverse strands 206 so as to deform the positions thereof when the force is applied. In this manner, needle holder 244 could be rotated to virtually any angle about strands 206 and still open clip retainer 204 with a compressive force. The compressive force is preferably applied using a standard needle holder 244 or forceps, although other tools could be used, preferably those with applicators narrower than the length of the shrink tube 210.

In some embodiments, elastically deformable material 234 may be made from a nickel titanium (nitinol) based alloy. Elastically deformable material 234 may include additional elements in addition to nitinol which affect the yield strength of the material or the temperature at which particular pseudoelastic or shape transformation characteristics occur. The transformation temperature may be defined as the temperature at which a shape memory alloy finishes transforming from martensite to austenite upon heating elastically deformable material 234 may exhibit pseudoelastic (superelastic) behavior when deformed at a temperature slightly above its transformation temperature. For example, if elastically deformable material 234 is a shape memory alloy, a portion of the shape memory alloy may be converted from its austenitic phase to its martensitic phase when the wire is in its deformed configuration. As the stress is removed, elastically deformable material 234 may undergo a martensitic to austenitic conversion and spring back to its original undeformed configuration. For example, elastically deformable material 234 may be formed as a shape memory alloy by first wrapping a wire onto a mandrel and heat treating the wire at approximately 400-500 degrees Celsius for approximately 5 to 30 minutes. Elastically deformable material 234 may be then air quenched at room temperature. The mandrel may have a constant diameter or may be conical in shape.

The position, pattern and number of electrodes carried by the various leads described in this disclosure may vary. For example, some leads may carry a single electrode or multiple electrodes. The electrodes may be arranged in a linear array, a two-dimensional array, or a three-dimensional array. The electrodes may take the form of electrode rings, pads, or probes. In addition, the leads may take the form of conventional axial leads with ring electrodes or paddle leads with a two-dimensional array of electrode pads.

Electrodes carried by a given lead may form bipolar or multipolar electrode combinations with electrodes on the same lead or electrodes on a different lead or leads. In addition, such electrodes may form unipolar electrode combinations with one or more electrodes carried by an implantable stimulation generator, e.g., on the housing or "can" in an active can arrangement. In addition, in some embodiments, an electrical stimulation generator may carry integrated electrodes, forming a so-called leadless stimulator or "microstimulator." In each of these cases, a deployable clip as described herein may be utilized to fix a lead, stimulation generator housing, or other implantable medical device relative to a desired target site for delivery of electrical stimulation, drugs or other therapies.

Various embodiments of the invention have been described. However, modifications can be made to the described embodiments without departing from the spirit and scope of the invention. For example, electrical stimulation leads with an actively deployable clip are described with respect to gastric stimulation, but electrical stimulation leads used for other forms of stimulation may also include integrated actively deployable clips. An electrical stimulation lead with an actively deployable clip may be used for cardiac stimulation, functional electrical stimulation, peripheral nerve stimulation, spinal cord stimulation, pelvic nerve stimulation, deep brain stimulation, or subcutaneous neurological stimulation as well as other forms of stimulation. In addition, gastric stimulation may include stimulation of any of a variety of sites along the gastrointestinal tract including the esophagus, lower esophageal sphincter, stomach, pyloric sphincter, small intestine, large intestine and colon.

Additionally, actively deployable clips may be integrated as part of any implantable medical device to secure the medical device in place after implantation. However, the invention may be particularity useful for minimally invasive implantation techniques such as laparoscopic or endoscopic procedures to reduce surgical time as described previously with respect to implantation of electrical stimulation leads. Examples of implantable medical devices that may include integrated actively deployable clips include electrical stimulation generators, leads, drug pumps, catheters, sensors, and replacement valves. Other implantable medical devices may also include integrated actively deployable clips.

These and other embodiments are within the scope of the following claims.

The invention claimed is:

1. A system comprising:
an implantable medical device including a lead carrying one or more electrodes;
a clip attached to the implantable medical device, wherein the clip is actively deployable from a first shape to a second shape to resist substantial movement of the implantable medical device from a target site within a body of a patient; and
a retainer comprising a plurality of strands releasably retaining an enlarged portion of the clip to hold the clip in the first shape,
wherein the clip includes:
a wire formed from one of an elastic material or a shape memory alloy material; and
a coil comprising a plurality of loops surrounding the wire, wherein the coil is held in a compressed state by the retainer to hold the clip in the first shape.

2. The system of claim 1, wherein the retainer releases the clip for deployment to the second shape in response to manipulation of the retainer.

3. The system of claim 2, wherein the retainer releases the clip in response to exertion of a compressive force on the retainer.

4. The system of claim 2, further comprising a needle attached to the clip retainer and thereby releasably attached to the clip.

5. The system of claim 2, wherein the first shape is a substantially straight shape.

6. The system of claim 2, wherein the second shape is a substantially curved shape.

7. The system of claim 2, wherein the second shape is a spiral shape.

8. The system of claim 1, further comprising an electrical stimulation generator coupled to the lead.

9. The system of claim 1, wherein the clip is attached to a distal end of the lead.

10. The system of claim 9, further comprising tines attached to a portion of the lead more proximate than the first clip.

11. The system of claim 1, further comprising an anchor disk having an aperture, wherein the clip extends through the aperture of the anchor disk.

12. A system comprising:
an implantable medical device including a lead carrying one or more electrodes;
a clip attached to the implantable medical device, wherein the clip is actively deployable from a first shape to a second shape to resist substantial movement of the implantable medical device from a target site within a body of a patient; and
a retainer comprising a plurality of strands releasably retaining an enlarged portion of the clip to hold the clip in the first shape,
wherein the clip is attached to a distal end of the lead,
wherein the clip is a first clip, the system further comprising a second clip attached to a portion of the lead more proximate than the first clip.

13. The system of claim 12, wherein the first clip includes:
a wire formed from one of an elastic material or a shape memory alloy material; and
a coil comprising a plurality of loops surrounding the wire, wherein the coil is held in a compressed state by the retainer to hold the first clip in the first shape.

14. The system of claim 12, wherein the retainer releases the clip in response to exertion of a compressive force on the retainer.

15. The system of claim 12, further comprising a needle attached to the retainer and thereby releasably attached to the clip.

16. The system of claim 12, further comprising an electrical stimulation generator coupled to the lead.

17. The system of claim 12, further comprising tines attached to a portion of the lead more proximate than the first clip.

18. The system of claim 12, further comprising an anchor disk having an aperture, wherein the clip extends through the aperture of the anchor disk.

19. A method comprising:
implanting an implantable medical device including a lead carrying one or more electrodes in a body of a patient; and
actively deploying a clip attached to the implantable medical device, wherein the clip is actively deployable from a first shape to a second shape to resist substantial movement of the implantable medical device from a target site within a body of a patient,
wherein actively deploying the clip comprises releasing the clip from a retainer comprising a plurality of strands releasably retaining an enlarged portion of the clip,
wherein the clip includes a wire formed from one of an elastic material or a shape memory alloy material,
wherein the implantable medical device comprises a coil comprising a plurality of loops surrounding the wire, wherein the coil is held in a compressed state by the retainer to hold the clip in the first shape.

20. The method of claim 19, further comprising applying a compressive force to the retainer to release the clip.

21. The method of claim 19, wherein the clip retainer is attached to a needle, the method further comprising releasing the needle with the retainer.

22. The method of claim 19, wherein the first shape is a substantially straight shape.

23. The method of claim 19, wherein the second shape is a substantially curved shape.

24. The method of claim 19, wherein the second shape is a spiral shape.

25. The method of claim 19, further comprising coupling an electrical stimulation generator to the lead.

26. The method of claim 19, wherein the clip is attached to a distal end of the lead.

27. The method of claim 19, further comprising extending a portion of the clip through an aperture of an anchor disk before deploying the clip.

28. A method comprising:
implanting an implantable medical device including a lead carrying one or more electrodes in a body of a patient; and
actively deploying a clip attached to the implantable medical device, wherein the clip is actively deployable from a first shape to a second shape to resist substantial movement of the implantable medical device from a target site within a body of a patient,
wherein actively deploying the clip comprises releasing the clip from a retainer comprising a plurality of strands releasably retaining an enlarged portion of the clip,
wherein the clip is attached to a distal end of the lead,
wherein the clip is a first clip, the method further comprising deploying a second clip attached to a portion of the lead more proximate than the first clip.

29. The method of claim 28, wherein actively deploying the clip comprises applying a compressive force to the retainer to release the clip.

30. The method of claim 28, wherein the clip retainer is attached to a needle, the method further comprising releasing the needle with the retainer.

31. The method of claim 28, further comprising coupling an electrical stimulation generator to the lead.

32. The method of claim 28, wherein the clip is attached to a distal end of the lead.

* * * * *